United States Patent [19]

Shum

[11] Patent Number: 4,764,628

[45] Date of Patent: Aug. 16, 1988

[54] ASYMMETRIC EPOXIDATION OF ALLYLIC ALCOHOLS

[75] Inventor: Wilfred P. Shum, Swarthmore, Pa.

[73] Assignee: ARCO Chemical Company, Newtown Square, Pa.

[21] Appl. No.: 95,973

[22] Filed: Sep. 14, 1987

[51] Int. Cl.$^4$ .................................. C07D 301/19
[52] U.S. Cl. ............................................ 549/529
[58] Field of Search ..................................... 549/529

[56] References Cited

U.S. PATENT DOCUMENTS

| | | | |
|---|---|---|---|
| 3,625,981 | 12/1971 | Kollar | 549/529 |
| 3,870,729 | 3/1975 | Bost et al. | 549/529 |
| 3,928,393 | 12/1975 | Herzog | 549/529 |
| 4,471,130 | 9/1984 | Katsuki et al. | 549/529 |
| 4,594,439 | 6/1986 | Katsuki et al. | 549/529 |

FOREIGN PATENT DOCUMENTS 0197766 10/1986 European Pat. Off. .

*Primary Examiner*—Norma S. Milestone
*Attorney, Agent, or Firm*—Lewis J. Young

[57] ABSTRACT

Asymmetric epoxidation of allylic alcohols using carboxylic acid treated phenethyl hydroperoxide oxidate and titanium tartrate catalyst gave optically active glycidols following an enantioselection rule opposite to that observed from the Sharpless epoxidation (U.S. Pat. No. 4,471,130). Overall yield and enantiomeric excess of the glycidol made are dependent on the amount of carboxylic acid present in the oxidate feed. This novel finding provides a direct epoxidation route to (R)-glycidol using the less expensive natural L-(+)-dialkyl tartrate ligand.

2 Claims, No Drawings

ASYMMETRIC EPOXIDATION OF ALLYLIC ALCOHOLS

BACKGROUND OF THE INVENTION

The present invention is directed to the asymmetric epoxidation of allylic alcohols.

U.S. Pat. No. 4,471,130 teaches to epoxidize allylic alcohols using titanium complexes containing optically active alkoxide ligands as catalyst in the presence of an alkyl hydroperoxide oxidate. This catalyst system always delivers the epoxide oxygen from the same enantioface of the olefin regardless of the substitution pattern. Thus, the use of L(+)-dialkyl tartrate leads to the formation of the (S)-glycidol, whereas the use of D(−)-dialkyl tartrate leads to the (R)-glycidol. Although this reaction provides a simple synthetic route to the desired epoxy alcohol enantiomers, the disadvantage of the method of the patent is that the D(−)-dialkyl tartrate is much more expensive than the natural L(+)-dialkyl tartrate.

BRIEF SUMMARY OF THE INVENTION

It has now been found that the isomer obtained with the natural, and inexpensive L(+)-dialkyl tartrate can be the (R)-glycidol if the ethylbenzene hydroperoxide oxidant is used in conjunction with a small amount of a carboxylic acid. None of the other alkyl hydroperoxides (alkyl=tert-butyl, cumyl, or trityl), when used with the carboxylic acid, gave good yield or good enantioselectivity.

DETAILED DESCRIPTION OF THE INVENTION

The process of this invention comprises reacting a mixture of an allylic alcohol, ethylbenzene hydroperoxide, a carboxylic acid and a metal catalyst consisting of titanium dialkyl tartrate in an organic solvent, and separating the product from the reactants.

The allylic alcohols suitable for use in the epoxidation reaction may have the following general formula:

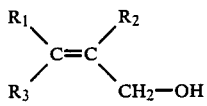

where $R_1$, $R_2$, and $R_3$ may be the same or different selected from H, $C_1$-$C_{10}$ linear or branched alkyl, phenyl, and substituted phenyl.

The only organic hydroperoxides useful in the invention is ethylbenzene hydroperoxide. Other hydroperoxides tried but not effective, are cumene hydroperoxide, tert-butyl hydroperoxide, and trityl hydroperoxide.

The metal catalysts useful in the invention include various salts of titanium, in conjunction with a chiral carbinol, such as diisopropyl tartrate. Particularly useful salts are the naphthenates, the isopropoxides, and other alkoxides.

The carboxylic acids which can be added with the ethylbenzene hydroperoxide to effect the reverse enantioselectivity (forming the (R)-glycidols) include formic acid, acetic acid, benzoic acid, and p-nitrobenzoic acid. Not all carboxylic acids are effective in the invention, however, since trifluoroacetic acid gave 40% enantiomeric excess of the (S)-glycidol derivative. Without the carboxylic acid addition, only the (S)-glycidol derivatives are obtained using the natural L(+)-dialkyl tartrate ligand. The amount of carboxylic acid added to effect the reverse enantioselectivity should be such that the ratio of titanium:acid is between 1:0.2 and 1:2.5.

The useful organic solvents may include hexane, toluene, tetrahydrofuran, methylene chloride, methyl acetate, and mixtures of these. The solvent also should not react with the reactants in the medium to interfere with the transfer of the oxygen atom from the oxidant to the allylic unsaturation.

The reaction temperature may vary from -100°C. to 20°C. and the times may vary from a few minutes to a few days.

The following examples are meant to further illustrate, but not to limit the invention.

EXAMPLE I

Comparative Example—Not This Invention

To a reaction flask at room temperature was charged 15 g (0.26 mole) of allyl alcohol, 3.8 g (0.016 mole) of L(+)-diisopropyl tartrate, 50 g (0.59 mole) of dichloromethane, and 10 g of 3A molecular sieves. After cooling to −15°C., 3.8 g (0.013 mole) titanium isopropoxide was added followed by 480 g of purified ethylbenzene hydroperoxide (EBHP) (14.8 wt % EBHP in ethylbenzene). After 20 hours at −15°C., the reaction was considered complete and a 65% glycidol yield was obtained from GC analysis. Optical purity of glycidol was determined by $^{13}$C NMR on the glycidyl Mosher ester prepared from homochiral α-methoxy-α-trifluoromethylphenylacetyl chloride and the glycidol actually isolated. The enantiomeric excess of the (S)-glycidol made was 60%.

EXAMPLE II

To a reaction flask at room temperature was charged 15 g (0.26 mole) of allyl alcohol, 3.8 g (0.016 mole) of L(+)-diisopropyl tartrate, 50 g (0.59 mole) of dichloromethane, and 10 g of 3A molecular sieves. After cooling to −15°C., 3.8 g (0.013 mole) titanium isopropoxide was added followed by 480 g of purified ethylbenzene hydroperoxide (EBHP) (14.8 wt % EBHP in ethylbenzene) which contained 0.79 g of benzoic acid.. After 20 hours at −15°C., the reaction was considered complete and a 49% glycidol yield was obtained from GC analysis. Optical purity of glycidol was determined by $^{13}$C NMR on the glycidyl Mosher ester prepared from homochiral α-methoxy-α-trifluoromethylphenylacetyl chloride and the glycidol actually isolated. The enantiomeric excess of the (R)-glycidol made was 68%.

EXAMPLE III

To show that the optical purity of the (R)-glycidol made in Example II can be improved, Example II was repeated with 480 g of EBHP which contained 1.6 g of benzoic acid. Glycidol yield after 20 hours at −15°C. was 35%, and the enantiomeric excess of the (R)-glycidol made was 80%.

EXAMPLE IV

To examine the effect of the titanium tartrate catalyst composition on allyl alcohol epoxidation, the titanium:L(+)-diisopropyl tartrate mole ratio was modified from 1:1.2 to 1:0.5. To a reaction flask at room temperature were charged 15 g (0.26 mole) of allyl alcohol, 1.6 g (0.0067 mole) of L(+)-diisopropyl tartrate, 50 g (0.59 mole) of dichloromethane, and 10 g of 3A molecular sieves. After cooling to −15°C., 3.8 g (0.013 mole) of titanium isopropoxide was added followed by 480 g of EBHP (14.8 wt % EBHP in ethylbenzene) which contained 1.6 g of benzoic acid. After 20 hours at −15°C., glycidol yield was 31% and the enantiomeric excess of the (R)-glycidol was 65%.

EXAMPLE V

To show that acetic acid can also effect reverse enantioselectivity, the 1.6 g of benzoic acid added to the EBHP oxidate feed in Example III was replaced with 0.79 g of glacial acetic acid. After 20 hours at −15°C., glycidol yield was 45% and the enantiomeric excess of (R)-glycidol was 75%.

EXAMPLE VI

The process of Example V was repeated by increasing the titanium:acetic acid mole ratio to 1:2.5 by adding 2.0 g of acetic acid to the EBHP oxidate feed. After 20 hours, glycidol yield was 42% and the enantiomeric excess of (R)-glycidol was 85%.

EXAMPLE VII

To show that formic acid is also effective in producing (R)-glycidol from L(+)-dialkyl tartrate, epoxidation was similarly carried out on 15 g of allyl alcohol using 480 g of the EBHP oxidate feed which contained 0.61 g of formic acid. Glycidol yield was 32% and the enantiomeric excess of (R)-glycidol was 71%.

EXAMPLE VIII

The process of Example II was repeated using EBHP oxidate feed treated with 2.2 g of p-nitrobenzoic acid in place of that treated with benzoic acid. The glycidol yield was 42% and the enantiomeric excess of (R)-glycidol was 62%.

EXAMPLE IX

Comparative Example—Not This Invention

When the benzoic acid of Example II was replaced with 0.45 g of trifluoroacetic acid, the reverse enantioselectivity was not observed. Glycidol yield was 40% and the enantiomeric excess of the (S)-glycidol was only 40%.

EXAMPLE X

Comparative Example—Not This Invention

To show that the acidified EBHP oxidate system is unique in obtaining reversed enantioselectivity, allyl alcohol epoxidation has been carried out with benzoic acid treated cumyl hydroperoxide. To a reaction flask at room temperature was charged 15 g (0.26 mole) of allyl alcohol, 3.8 g (0.016 mole) of L(+)-diisopropyl tartrate, 120 g (1 mole) of cumene, and 10 g of 3A molecular sieves. After cooling to −15°C., 3.8 g (0.013 mole) titanium isopropoxide was added followed by 109 g of purified cumyl hydroperoxide (80% in cumene) which contained 1.6 g of benzoic acid.. After 20 hours at −15°C., the reaction was considered complete and a 30% glycidol yield was obtained from GC analysis. Optical purity of glycidol was determined by $^{13}C$ NMR on the glycidyl Mosher ester prepared from homochiral α-methoxy-α-trifluoromethylphenylacetyl chloride and the glycidol actually isolated. The enantiomeric excess of the (S)-glycidol made was 20% with no reversed enantioselectivity.

EXAMPLE XI

Comparative Example—Not This Invention

Example X was repeated using acid-free cumyl hydroperoxide. Glycidol yield was 72% and the enantiomeric excess of (S)-glycidol was 90%

EXAMPLE XII

To show that the acidified EBHP is also effective in reversing the enantioselectivity in the epoxidation of allylic substrates other than allyl alcohol, similar reaction was carried out on cinnamyl alcohol.

To a reaction flask at room temperature was charged 34 g (0.26 mole) of cinnamyl alcohol, 7.4 g (0.031 mole) of L(+)-diisopropyl tartrate, 130 g (1.5 mole) of dichloromethane, and 10 g of 3A molecular sieves. After cooling to −15°C., 7.6 g (0.026 mole) titanium isopropoxide was added followed by 203 g of purified ethylbenzene hydroperoxide (EBHP) (35 wt % EBHP in ethylbenzene) which contained 0.79 g of benzoic acid.. After 20 hours at −15°C., the solution was worked up and the product contained a 20% enantiomeric excess of the (2R,3R)-epoxycinnamyl

EXAMPLE XIII

Comparative Example—Not This Invention

Example XII was repeated using acid-free EBHP oxidate. The isolated product had a 95% enantiomeric excess of the (2S, 3S)-epoxycinnamyl alcohol.

We claim:

1. In a process for the asymmetric epoxidation of allylic alcohols of the general formula:

$$\begin{array}{c} R_1 \\ \phantom{R_1}\diagdown \\ \phantom{R_1R_1}C=C \\ \phantom{R_1}\diagup \\ R_3 \end{array} \begin{array}{c} R_2 \\ \diagup \\ \\ \diagdown \\ CH_2-OH \end{array}$$

where $R_1$, $R_2$, and $R_3$ may be the same or different selected from H, $C_1$–$C_{10}$ linear or branched alkyl, phenyl, and substituted phenyl, comprising reacting in an organic solvent said allylic alcohol with from 4 to 15 parts of ethylbenzene hydroperoxide, and from 0.013 to 0.026 parts of a catalyst made from essentially equimolar mixtures of titanium tetraisopropoxide and L-(+)-diisopropyl tartrate, the improvement comprising treating the hydroperoxide with a carboxylic acid selected from the group consisting of formic acid, acetic acid, benzoic acid, and p-nitrobenzoic acid in a ratio of titanium:acid of between 1:0.2 and 1:2.5 whereby the epoxide product has an enantiomeric excess of the (R)-glycidol isomer.

2. The process of claim 1 wherein the organic solvents are selected from the group consisting of hexane, toluene, tetrahydrofuran, methylene chloride, methyl acetate, and mixtures of these.

* * * * *